United States Patent [19]

Mori et al.

[11] Patent Number: 5,047,270

[45] Date of Patent: Sep. 10, 1991

[54] COATED RESIN MOLDED-ARTICLE

[75] Inventors: Shigeo Mori, Tokyo; Atsunori Yaguchi; Masahiro Kitayama, both of Sodegaura, all of Japan

[73] Assignee: Idemitsu Petrochemical Company Limited, Tokyo, Japan

[21] Appl. No.: 244,216

[22] Filed: Sep. 14, 1988

[30] Foreign Application Priority Data

| Sep. 14, 1987 | [JP] | Japan | 62-230485 |
| Sep. 14, 1987 | [JP] | Japan | 62-230486 |
| May 13, 1988 | [JP] | Japan | 63-114738 |
| Jun. 9, 1988 | [JP] | Japan | 63-142617 |
| Jun. 9, 1988 | [JP] | Japan | 63-142618 |
| Jun. 9, 1988 | [JP] | Japan | 63-142619 |
| Jun. 9, 1988 | [JP] | Japan | 63-142637 |
| Jun. 9, 1988 | [JP] | Japan | 63-142638 |
| Jun. 9, 1988 | [JP] | Japan | 63-142639 |
| Jun. 22, 1988 | [JP] | Japan | 63-154020 |

[51] Int. Cl.$^5$ .................... B32B 27/36; B65D 53/00; C08J 9/10
[52] U.S. Cl. .................. 428/35.2; 428/412; 428/480; 428/35.7; 264/DIG. 33; 264/209.1; 426/106; 427/54.1
[58] Field of Search .............. 428/480, 412, 900, 35.2, 428/35.7

[56] References Cited

U.S. PATENT DOCUMENTS

| 3,551,202 | 12/1970 | Wright et al. | 428/463 |
| 4,026,839 | 5/1977 | Dieck | 525/474 |
| 4,728,345 | 3/1988 | Murphy | 55/158 |
| 4,812,360 | 3/1989 | Utsumi | 428/480 |
| 4,818,577 | 4/1989 | Ou-Yang | 428/480 |
| 4,820,581 | 4/1989 | Saito et al. | 428/480 |

FOREIGN PATENT DOCUMENTS

| 0004862 | 11/1979 | European Pat. Off. |
| 57-131214 | 8/1982 | Japan . |
| 58-1756 | 1/1983 | Japan . |
| 59-2449 | 1/1984 | Japan . |
| 61-47406 | 3/1986 | Japan . |
| 2046627 | 11/1980 | United Kingdom . |

OTHER PUBLICATIONS

Database WPIL (Derwent), No. 88-326897 (46), Derwent Publications Ltd, London, GB: & JP-A-63 241 075 (Idemitsupetrochemical K.K.) *Whole Article* & Cited Against the Right of Priority.

Primary Examiner—P. C. Sluby
Attorney, Agent, or Firm—Armstrong, Nikaido, Marmelstein, Kubovcik & Murray

[57] ABSTRACT

Provided herein is a coated resin molded-article which comprises a polyester resin substrate and a cured coating formed thereon which contains a curable phosphazene compound. The molded article will find use as film, sheet, and container which have improved abrasion resistance, weather resistance, heat resistance, heat shock resistance, hot water resistance, moisture resistance, alkali resistance, impact resistance, cloud resistance, transparency, oil resistance, surface gloss, and air barrier properties, while keeping the good properties of the resin.

8 Claims, 2 Drawing Sheets

COATED RESIN MOLDED-ARTICLE

BACKGROUND OF THE INVENTION

1. Field of the Invention

The present invention relates to a coated resin molded-article. More particularly, it is concerned with a coated polyester resin molded-article in which a cured coating is formed on the surface of a desired polyester resin substrate, said coating can be formed on the surface of a polyester resin substrate by a simple process in a short time, has good adhesion to the surface of a polyester resin substrate, permits a polyester resin substrate to be flexible, has good mechanical properties which improve the hardness and scratch resistance of the surface of a polyester resin substrate, and has superior optical, thermal, and chemical properties.

The coated resin molded-article pertaining to the present invention, especially in the case where the resin molded article is a polyester molded article, has good durability on account of the cured coating having the above-mentioned superior properties. Therefore, it will find use in broad application areas including masks used in the production of ICs and printed circuits, base film for printing, base film for magnetic recording media, base film for heat-sensitive transfer recording media, glass substitute, and vacuum electron tubes.

2. Description of the Related Art

A polyester resin, for example, polyethylene terephthalate, has good flexibility, mechanical properties (such as strength), and optical properties. Therefore, it finds use as film and sheet, fiber, and other materials in a wide range of applications.

Another polyester resin, for example, polycarbonate, has high mechanical strength (especially impact strength), heat resistance, and transparency, and is light in weight. Therefore, it is often used as a glass substitute.

Unfortunately, polyester resins are not necessarily satisfactory in surface properties such as hardness, scratch resistance, adhesion resistance, heat resistance, and chemical resistance, when used in certain application areas. For improvement of surface properties, the surface of polyester resin articles are provided with a coating. There has been a demand for the development of a good coating because the improvement of surface properties is important in such application areas as photomask base film used for the production of ICs and printed circuits in the electronics industry, base film used for printing pattern, base film for magnetic recording media and heat-sensitive transfer recording media, and functional coatings to be made on such base film.

There are known, for coating polyester resin molded-articles, material such as acrylic hard coat and silicone hard coat.

The conventional coating materials have some disadvantages when applied to polyester; they do not readily form a coating with good adhesion by a single application (or one coating). To eliminate this disadvantage, it is necessary to treat the surface of the article to be coated by corona discharge or with primer, or to repeat application of the coating twice or more. These additional steps make the coating process more complex and longer.

It may safely be said that heretofore there was no coated resin molded-article in which good coating was formed on the surface of polyester molded-article by a single application of a coating material without any preliminary surface treatment.

Even though it was possible to form a suitable coating on the surface of polyester molded article by repeated application, the resulting polyester molded article had its inherent shortcomings mentioned below.

In the case where polyethylene terephthalate (a kind of polyester) is used as a base film for ink ribbon, it is provided with a backing layer (on the opposite side of the ink layer) which is formed by the application of a coating material of thermosetting silicone. This backing layer is necessary to prevent blocking and sticking. A disadvantage of the ink ribbon with backing layer is that some components in the backing layer migrate into the ink layer when the ink ribbon is left wound for a long period of time. The result of such migration is that the ink ribbon does not print sharp and clear letters.

Also, in the case where polyethylene terephthalate is used as base film for audio and video magnetic tape, it is provided with a backing layer, on the opposite side of the magnetic layer, for the purpose of smooth tape running. A disadvantage of magnetic tape of this type is that adhesion between the base film and the backing layer is not sufficient and the backing layer is not satisfactory in scratch resistance and durability.

Polyester resins (such as polyethylene terephthalate, polybutylene terephthalate, and polycarbonate) are used for a large variety of containers. Containers of these polyester resins have recently been used for storing petroleum products, chemicals, pesticides, and detergents, or packaging foods and drinks. Some of them, with a food packaged therein are heated in an electronic oven for cooking. These containers, therefore, are required to have good heat resistance, chemical resistance, and surface hardness.

On the other hand, polycarbonate (a kind of polyester resin) has found use as a glass substitute because of its good mechanical strength (especially high impact strength), heat resistance, and transparency. Applications of polycarbonate include automotive window glass and light cover, building glazing, plastic mirror with metallic film backing, and casings of appliances such as dish washers, humidifiers, coffee makers, sake warmers, and steam irons which use hot water, cold water or steam.

The polycarbonate used as automotive window glass and light cover and building glazing is required to have a cured coating so that it has improved weather resistance, oil resistance, and scratch resistance. An example of the cured coating is one which is formed by irradiating, with ultraviolet rays, a composition composed of acrylate compound, silane compound or silane, silica, and photopolymerization initiator. (See Japanese Patent Laid-open Nos. 131214/1982 and 1756/1983.) However, the weather resistance imparted by such a coating is inferior to that of glass. In addition, the cured coating is liable to hold water droplets when exposed to rain. The water droplets, like lenses, locally intensify the sunlight, causing degradation of the resin molded article. This accelerates the degradation of the originally insufficient weather resistance of the resin molded-article.

Incidentally, it is known that a phosphazene compound which cures upon polymerization is used as a dental filler or adhesive. (See Japanese Patent Laid-open No. 47406/1986.) This publication discloses a phosphazene compound composed of units represented by the formula below.

—[NP (X) (Y)]$_n$— where n is 3 to 18, preferably 3 and 4; (X)+(Y)=2; (X) and (Y) are each above 0; (X) and (Y) are identical or (Y) is chlorine or a mixture containing chlorine; and (X) is —O(CH$_2$R)O$_2$CCCH$_3$=CH$_2$ [where R is an alkyl group having 1 to 11 carbon atoms].

According to the disclosure, the phosphazene compound has a high thermal decomposition point and it provides, upon polymerization, a cured product which resembles an inorganic compound in having high rigidity and hardness and a small coefficient of thermal expansion. It is a useful dental resin.

There is disclosed in Japanese Patent Publication No. 2449/1984 a process for producing a polyfunctional (meth)acrylate phosphazene polymer in a non-gel form. According to the disclosure, the process comprises reacting, in the presence of a catalyst, (A) a chlorinated phosphazene polymer containing about 71 wt% or less, preferably about 4 to 55 wt%, of chlorine, with one or more than one functional acrylic monomer selected from the group consisting of (B) acrylamide or methacrylamide, (C) an acrylate or methacrylate having one hydroxyl group, and (D) alkylsubstituted acrylamide or methacrylamide having one hydroxyl group, or further reacting the thus obtained reaction product with one or more than one inert compound selected from the group consisting of (E) a monohydric alcohol having 1 to 18 carbon atoms, (F) a monohydric thioalcohol, (G) a monohydric phenol, and (H) a compound having a primary or secondary amino group. The reaction changes the chlorinated phosphazene polymer into a polyfunctional acrylate or methacrylate phosphazene polymer in a non-gel form of which has at least two acryl or methacryl groups.

The official gazette publication also discloses the following: The (meth)acrylate phosphazene polymer produced according to the process disclosed in the official gazette can be made, upon curing, into a crosslinked polymer, which is an inorganic polymer, having outstanding heat resistance. The polymer is flexible if long-chain (meth)acrylate phosphazene is used as the starting substance Moreover, the polymer has outstanding heat resistance if the above-mentioned inert compound is a halogenated monoalcohol, phenol, or benzyl alcohol. By virtue of these characteristic properties, the (meth)acrylate phosphazene polymer finds use as a coating material and adhesive for a variety of substrates, such as metal, plastics, glass, wood, paper, fiber, and rubber, and also as a raw material or substrate for molded articles, printing inks, printing plates, and gaskets.

SUMMARY OF THE INVENTION

It is an object of the present invention to provide a coated resin molded-article having extremely improved durability. According to the present invention, the coating is formed on the surface of a desired polyester resin substrate by a single application without surface treatment or primer coating. The thus formed coating has good adhesion, high surface hardness and scratch resistance, good chemical and heat resistance, and good optical properties. Moreover, according to the present invention, the coating can be formed by a very simple manner in a short time.

It is another object of the present invention to provide a coated resin molded-article which is produced by covering a polyester substrate with a coating for functional characteristics as well as protection. The coating has many functions, such as good adhesion, surface properties, magnetic properties, and electrically conductive properties.

It is a further another object of the present invention to provide a coated resin molded-article which is suitable as a glass substitute on account of its improved surface hardness, scratch resistance, chemical resistance, heat resistance, and optical properties.

The present inventors carried out extensive studies on a coated resin molded-article with coating film or functional film which has good quality and the above-mentioned characteristic properties such as good durability. As the result, it was found that (1) the coating film or functional film can be formed on a polyester resin substrate in an extremely simple manner from a specific curable compound, (2) the thus formed coating film does not adversely affect the good properties of the polyester resin's own, and (3) the coating film is superior in adhesion to the polyester resin substrate and improves the surface properties (hardness and scratch resistance) of the polyester resin substrate. In addition, the coating film or functional film is superior in mechanical, optical, chemical, thermal, and protecting properties. These findings led to the present invention.

Accordingly, the gist of the present invention resides in a coated resin molded-article which comprises a polyester resin substrate and a cured coating formed thereon from a coating material containing a curable phosphazene compound.

Figure 1:
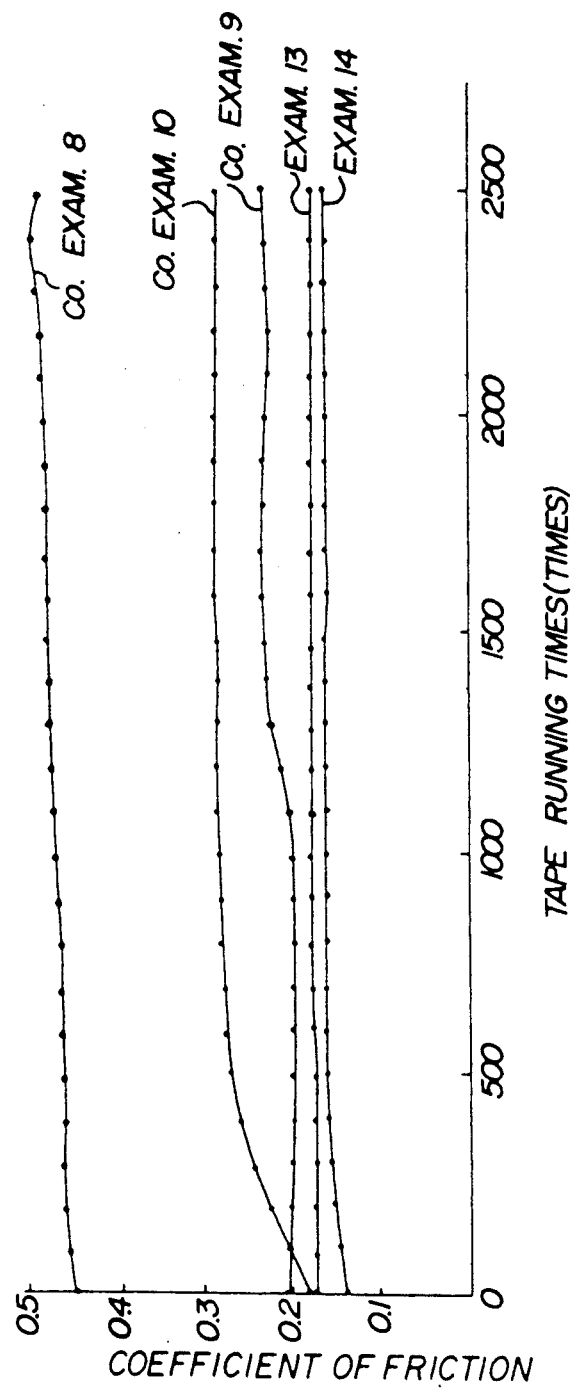
FIG. 1 and FIG. 2 are graphs in which the coefficient of friction is plotted against the tape running speed for tape samples obtained in examples and comparative examples.

Number 1 represents a tape film and number 2 represents presents a cylindrical drum.

DESCRIPTION OF THE PREFERRED EMBODIMENTS

The invention will be described in more detail in the following.

(1) Polyester resin substrate

The above-mentioned polyester resin substrate used in the present invention is not specifically limited. It includes polyester, polycarbonate, resin compositions thereof, and composite materials thereof reinforced with a filler or fiber.

Examples of the polyester include polyalkylene terephthalate (such as polyethylene terephthalate and polybutylene terephthalate), aromatic polyester, and thermosetting unsaturated polyester resin Examples of the polycarbonate usually include those which are obtained by reacting bisphenol-A with phosgene (or carbonate ester). The polycarbonate may contain a substituent group such as halogen and alkyl group. The polycarbonate also includes polyester carbonate.

The polycarbonate should preferably have as good transparency as possible if the coated resin molded-article of the present invention is to be used as a glass substitute In other words, in such a case, it is necessary to select a polycarbonate of good transparency for the polyester resin substrate.

The polyester resin substrate may be in any form, such as film, tape, sheet, plate, fiber, block, container and tube. The polyester resin substrate may be one which is used alone as a molded article or one which is used as a part of a molded article of other material.

The shape of the polyester resin substrate is determined according to the intended use of the coated resin molded-article.

The coated resin molded-article may be used as heat-sensitive transfer recording media (such as ink ribbon for a printer of a word processor) and magnetic recording media (such as audio and video magnetic tape). In such a case, the polyester resin substrate should preferably be in the form of tape. In the case where the coated resin molded-article is used for floppy disks, the polyester resin substrate should be in the form of a disk.

In the case where the coated resin molded-article is used for heat-sensitive transfer recording media (such as ink ribbon) and magnetic recording media, the thickness of the polyester resin substrate should be approximately equal to that of the conventional base film for them, although there are no specific limitations.

The coated resin molded-article of the present invention may also be used as lithfilm and photomask. In such a case, the polyester resin substrate should be in the form of sheet or film.

The coated resin molded-article may also be used as a laminate and as a container such as cup, dish and bottle. In the case where the coated resin molded-article is used as a container, the polyester resin substrate should have the same shape as the container. For example, if the container is a bottle, the coated polyester resin substrate should also be in the form of bottle. Containers in the form of bag or paper pack for food packaging may be formed by heat bonding the coated polyester resin sustrate in the form of multiple or single layered film.

In the case where the coated resin molded-article is used as a glass substitute, the resin substrate should be made of polycarbonate and it should be in the same form as the glass for which it is to be substituted. For example, if the coated resin molded-article is used as a glass substitute for building glazing, the resin substrate should be in the same form as the glazing. If the coated resin molded-article is used as a glass substitute for automotive window glass, light cover, and mirror, the resin substrate should be in the same form as window glass, light cover, and mirror to be substituted.

In the case where the coated resin molded-article is used as casing of various products, for example, color display tube, cathode ray tube, and fluorescent light tube, the resin substrate should be in the same form as such casing.

The coated resin molded-article of the present invention is characterized in that the above-mentioned polyester resin substrate has applied thereon a coating comprising a curable phosphazene compound.

(2) Coating

The coated resin molded-article of the present invention comprises a polyester resin substrate and a coating formed thereon from a coating material containing a curable phosphazene compound mentioned later.

The coating may be formed from one or more than one phosphazene compound mentioned later, or from a composition containing one or more than one phosphazene compound. In other words, the above-mentioned coating may be formed from a composition of curable phosphazene compound which is composed of one or more than one curable phosphazene compounds and other curable compounds such as polymerizable monomer, polymerizable prepolymer, urethane compounds, epoxy compounds, silicone compounds, and organotitanium compounds. The phosphazene compound or the composition of a phosphazene compound, may be incorporated, as required, with a cure accelerator such as polymerization initiator or thermal polymerization initiator, diluent, organic or inorganic filler, and other additives.

These cure accelerator, diluent, filler, and additives improve the formability of the coating and the mechanical and thermal properties of the resulting cured coating. It is possible to impart desired functional properties to the cured coating if an adequate filler is selected.

The coated resin molded-article of the present invention is composed of a desired polyester resin substrate and a cured coating formed thereon which contained, when it was coated on the substrate and before it was cured, at least the above-mentioned curable phosphazene compound. This coating may be formed from the curable phosphazene compound as such or from a composition of a curable phosphazene compound which comprises a curable phosphazene compound and other curable compounds or compositions. In addition, if necessary, the curable phosphazene compound, or a composition thereof, may have incorporated therewith a cure accelerator, such as photopolymerization initiator or thermal polymerization initiator, and organic filler and/or inorganic filler. The curable phosphazene compound or a composition thereof may be dissolved or dispersed in a diluent, and the resulting solution or dispersion may be applied to the polyester resin substrate to form a coating film, which is subsequently cured. Curable phosphazene compound The curable phosphazene compound is a compound represented by the formula below.

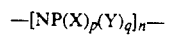  (I)

where X and Y each denote the same or a mutually different polymerizable-curable group or non-polymerizable-curable group (with at least one of them being a polymerizable-curable group); p and q each denote a numeral of 0 or above, with, the sum thereof being 2; and n denotes an integer of at least 3.

The polymerizable-curable group in the above-mentioned formula (I) is not specifically limited so long as it is a group having an unsaturated bond which is capable of polymerization by a chemical curing agent, heating, or irradiation with ultraviolet rays, visible light, or electron rays. Examples of the group include those groups containing an acryloyl group, a methacryloyl group, a vinyl group, and an allyl group.

The non-polymerizable-curable groups include, for example, a phenoxy group, a halogenated phenoxy group, an alkoxy group, a halogenated alkoxy group, an alkylamino group, a halogen group and a halogenated alkylamino group.

According to the present invention, the preferred examples of X and Y are acryloyloxy groups or methacryloyloxy groups represented by the formula below.

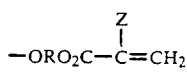 (II)

where R denotes an alkylene group having 1 to 12 carbon atoms and Z denotes a hydrogen atom or methyl group.

In the above formula (II), R may be a straight-chain or branched-chain alkylene group. A preferred alkylene group is an ethylene group.

Examples of the group represented by the above formula (II) are as follows: Residues formed by eliminating a hydrogen atom from the hydroxyl group in a methacrylate such as 2-hydroxyethyl methacrylate, 2-hydroxypropyl methacrylate, 2-hydroxybutyl methacrylate, 3-hydroxybutyl methacrylate, 4-hydroxybutyl methacrylate, 5-hydroxypentyl methacrylate, 6-hydroxy-3-methylhexyl methacrylate, 5-hydroxyhexyl methacrylate, 3-hydroxy-2-t-butylpropyl methacrylate, 3-hydroxy-2,2-dimethylhexyl methacrylate, 3-hydroxy-b 2-methylethylpropyl methacrylate, and 12-hydroxyldodecyl methacrylate. The residue may be referred to as methacrylate residue hereinafter, and residues formed by eliminating a hydrogen atom from the hydroxyl group in an acrylate such as 2-hydroxyethyl acrylate, 2-hydroxypropyl acrylate, 2-hydroxybutyl acrylate, 3-hydroxybutyl acrylate, 4-hydroxybutyl acrylate, 5-hydroxypentyl acrylate, 6-hydroxy-3-methylhexyl acrylate, 5-hydroxyhexyl acrylate, 3-hydroxy-2-t-butylpropyl acrylate, 3-hydroxy-2,2-dimethylhexyl acrylate, 3-hydroxy-2-methylethylpropyl acrylate, and 12-hydroxyldodecyl acrylate. Particularly preferable among them are 2-hydroxyethyl methacrylate residues and 2-hydroxyethyl acrylate residue.

The functional group containing the acryloyl group or methacryloyl group is not limited to those represented by the formula (II) above. That is, it may be the one represented by the formula (III) or the formula (IV).

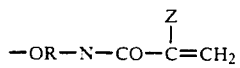 (III)

(where Z and R are defined as above.) This is the residue formed by removing a hydrogen atom from the hydroxyl group in hydroxyalkyl substituted (metha)acrylamide.

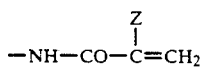 (IV)

(where Z is defined as above.) This is the residue formed by eliminating a hydrogen atom from the amino group in acrylamide or methacrylamide.

The allyl group-containing functional group include, in addition to allyl group itself, allyloxy group (CH$_2$=CH—CH$_2$O—) and other functional groups represented by the formulas below.

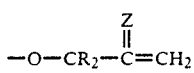 (V)

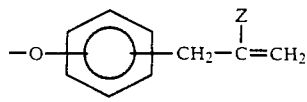 (VI)

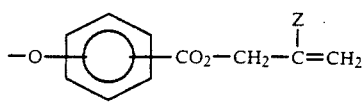 (VII)

(where Z and R are defined as above; and the two R groups may be the same or different.) These functional groups are formed by eliminating a hydrogen atom from the hydroxyl group of a compound, such as an aryl compound, having one hydroxyl group.

Examples of the functional groups represented by the formulas (V) to (VII) include the residues formed by eliminating a hydrogen atom from the hydroxyl group of an acryl compound represented by the following formulas.

CH$_2$=CH—CH$_2$—OH
CH$_2$=CH—CH(CH$_3$)—OH

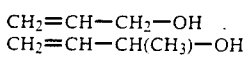

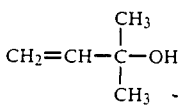

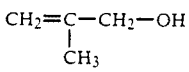

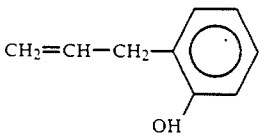

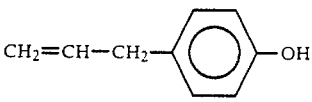

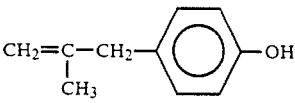

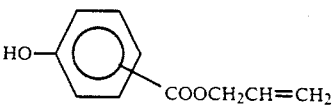

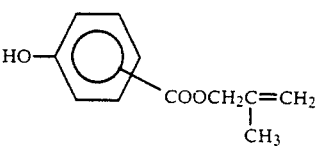

Examples of the non-polymerizable-curable group in the formula (I) include the group represented by the formula (VIII) below

R'M— (VIII)

or the group represented by the formula (IX) below

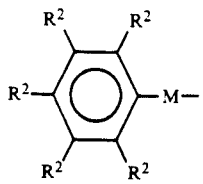
(IX)

where M in the formula (VIII) denotes an oxygen atom, sulfur atom, or imino group; and $R^1$ denotes an alkyl group having 1 to 18 carbon atoms or a halogenated alkyl group having 1 to 18 carbon atoms. Examples of $R^1$ include alkoxy groups (such as methoxy group, ethoxy group, propoxy group, butoxy group, pentyloxy group, hexyloxy group, heptyloxy group, and octyloxy group), alkoxy groups substituted with a halogen (such as fluorine, chlorine, and bromine), alkylthio groups (such as methylthio group, ethylthio group, propylthio group, butylthio group, pentylthio group, heptylthio group, and octylthio group), alkylthio groups substituted with a halogen (such as fluorine, chlorine, and bromine), alkylimino groups (such as methylimino group, ethylimino group, propylimino group, butylimino group, pentylimino group, hexylimino group, heptylimino group, and octylimino group), and alkylimino groups substituted with a halogen (such as fluorine, chlorine, and bromine); M in the formula (IX) is defined as above; the five $R^2$s are the same or different and may respectively denote a hydrogen atom, halogen atom, alkyl group having 1 to 4 carbon atoms, and halogenated alkyl group having 1 to 4 carbon atoms.

Examples of the group represented by the formula (IX) include a phenoxy group, a thiophenyl group, a halogenated phenoxy group (such as 2,4,6-tribromophenoxy group, a 4-broromophenoxy group, a 2-chlorophenoxy group, and a 2,4-dichlorophenoxy group), a halogenated thiophenyl group (such as a 4-chlorophenylthio group), and the residue formed by eliminating a hydrogen atom from the amino group in aniline or halogenated aniline (such as 2-chloroaniline, 2,4-dichloroaniline, 2,4,6-tribromoaniline).

The phosphazene compound in the present invention is one which has the repeating unit represented by the above formula (I). It should have a degree of polymerization of 3 or above, preferably 3 to 10,000, more desirably 3 to 18, and most desirably 3 or 4 (or a mixture thereof). The phosphazene compound may be one in which the repeating units represented by the formula (I) are bound to one another (polymerized) in a straight chain. However, the phosphazene compound should preferably be one in which the repeating units are bound to one another (polymerized) in a ring.

Examples of the phosphazene compound include the following.

Cyclic compounds represented by the formula below.

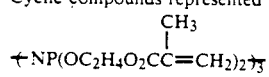

Cyclic compounds represented by the formula below.

$\{NP(OCH_2CH=CH_2)_2\}_{\overline{3}}$

Cyclic compounds represented by the formula below.

$\{NP(OC_2H_4O_2CCH=CH_2)_2\}_{\overline{3}}$

Cyclic compounds represented by the formula below.

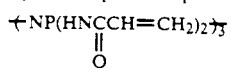

Cyclic compounds represented by the formula below.

$\{NP\{(OCH_2CH_3)(OC_2H_4O_2CCH=CH_2)\}\}_{\overline{3}}$

Cyclic compounds represented by the formula below.

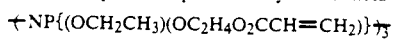

Cyclic compounds represented by the formula below.

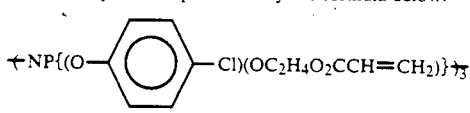

Cyclic compounds represented by the formula below.

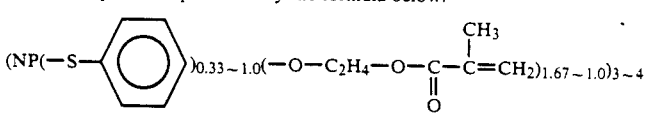

Cyclic compounds represented by the formula below.

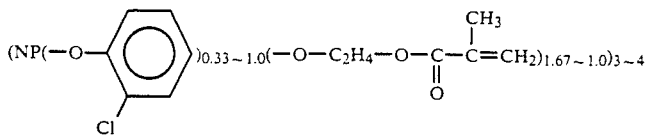

Cyclic compounds represented by the formula below.

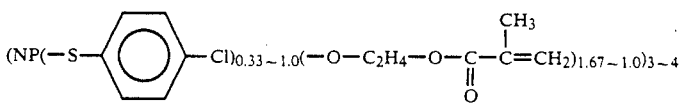

Cyclic compounds represented by the formula below.

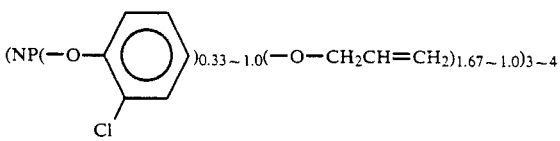

The above-listed phosphazene compounds can be prepared by various processes which are not specifically limited. For example, if it is desirable to introduce a group represented by the formula (II) as the polymerizable-curable group, a hydroxyalkyl (meth)acrylate corresponding to the formula (II) is used which is represented by the formula below.

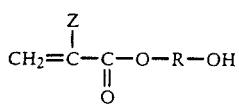

where R and Z are defined as above.

Or, if it is desirable to introduce a group represented by the formula (III) as the polymerizable-curable group, a hydroxyalkyl (meth)acrylamide corresponding to the formula (III) is used which is represented by the formula below.

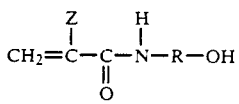

where R and Z are defined as above.

Or, if it is desirable to introduce a group represented by the formula (IV) as the polymerizable-curable group, a (meth)acrylamide corresponding to the formula (IV) is used which is represented by the formula below.

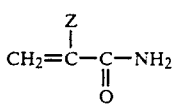

Or, if it is desirable to introduce a group represented by the formulas (V) to (VII) as the polymerizable curable group, an allyl alcohol, allyl phenol, allyl ester of hydroxybenzoic acid, or a derivative thereof corresponding to them is used which is represented by the formulas below.

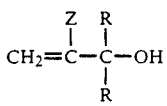

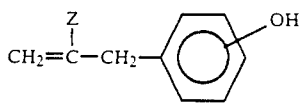

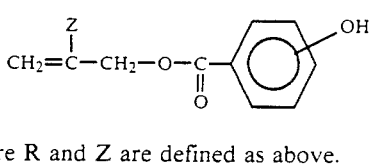

where R and Z are defined as above.

The group represented by the formula (VIII) which is introduced as the non-polymerizable-curable group differs depending on the atom or group denoted by M. If M denotes an oxygen atom, it is an alkanol or halogenated alkanol, or a derivative thereof represented by the formula below.

$R^1OH$ where $R^1$ is defined as above.

If M denotes a sulfur atom, it is an alkylmercaptan or halogenated alkylmercaptan, or a derivative thereof represented by the formula below.

$R^1SH$ where $R^1$ is defined as above.

If M denotes an imide group, it is an alkylamine or halogenated alkylamine, or a derivative thereof represented by the formula below.

$R^1NH_2$ where $R^1$ is defined as above.

The group represented by the formula (IX) which is introduced as the non-polymerizable-curable group differs depending on the atom or group denoted by M. If M denotes an oxygen atom, it is a phenol represented by the formula below.

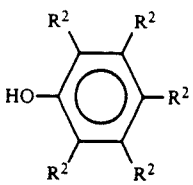

where $R^2$ is defined as above.

If M denotes a sulfur atom, it is a thiophenol represented by the formula below.

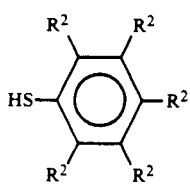

where $R^2$ is defined as above.

If M denotes an imide group, it is an aniline or a derivative thereof represented by the formula below.

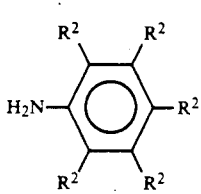

where $R^2$ is defined as above.

To obtain the desired phosphazene compound represented by the formula (I), the compound from which the polymerizable-curable group is formed and the compound to form the non-polymerizable-curable group are reacted with a chlorophosphazene (which is a cyclic compound represented by the formula $(NPCl_2)_n$ or a straight-chain compound represented by the formula $Cl_4P\cdot(NPCl_2)_{n-1}\cdot NPCl_3$, where n is 3 or above, preferably 3 to 18).

In the case where the compound to form the non-polymerizable-curable group is an alcohol, mercaptan, phenol, or thiophenol, they should preferably be changed beforehand into an alcoholate, phenolate, mercaptide, or thiophenolate, respectively, by the reaction with an alkali metal such as metallic sodium or metallic potassium.

When the compound from which the above-mentioned substituent group ill be formed, which contain amino imino or mercapte group is reacted with the chlorophosphazene, it is desirable to use a tertiary amino or the like to eliminate hydrogen halide. Examples of the tertiary amine include trimethylamine, triethylamine, triisopropylamine, tri-n-propylamine, tri-n-butylamine, pyridine, and picoline Preferable among them is pyridine.

Usually, this reaction is performed in an organic solvent. Examples of the organic solvent include benzene, toluene, xylene, chloroform, cyclohexane, methylene chloride, tetrahydrofuran, and 1,4-dioxane. They may be used individually or in combination with one another.

In the meantime, according to the present invention, the phosphazene compound is produced from a chlorophosphazene compound. The chlorophosphazene compound starting material should preferably be a trimer of dichlorophosphazene (hexachlorocyclotriphosphazene), a tetramer of dichlorophosphazene (octachlorocyclotetraphosphazene), or an oligomer thereof. The reason for this is that the trimer, tetramer, or oligomer provides a phosphazene compound which permits easy control of crosslink density in the coating (a cured product of the phosphazene compound).

Polymerizable monomer

Examples of the above-mentioned polymerizable monomers include monofunctional monomers (such as methyl methacrylate, 2-ethylhexyl acrylate, 2-hydroxyethyl acrylate, and 2-hydroxypropyl acrylate), difunctional compounds (such as 1,3-butanediole diacrylate, 1,4-butanediol diacrylate, 1,6-hexanediol diacrylate, ethyleneglycol diacrylate, diethyleneglycol diacrylate, triethyleneglycol diacrylate, tetraethyleneglycol diacrylate, neopentylglycol diacrylate, polyethyleneglycol diacrylate, hydroxypivalic acid ester, and neopentylglycol diacrylate), and trifunctional or multiple functional compounds (such as trimethylolpropane triacrylate, pentaerythritol acrylate, dipentaerythritol hexaacrylate, and triallyl isocyanate.

Polymerizable prepolymer

Examples of the polymerizable prepolymers include polyester acrylate, polyurethane acrylate, epoxy acrylate, polyether acrylate, melamine acrylate, oligoacrylate, alkyl acrylate, polyol acrylate, and silicone acrylate which contain at least one acryloyl group. Important among them are polyester acrylate, epoxy acrylate, and polyurethane acrylate. The polyester acrylate is produced by acrylating a polyester of a polyhydric alcohol and a polybasic acid. Examples of the polyhydric alcohol include ethylene glycol, 1,4-butanediol, 1,6-hexanediol, diethyleneglycol, trimethylolpropane, dipropylene glycol, polyethylene glycol, polypropylene glycol, pentaerythritol, and dipentaerythritol. Examples of the polybasic acid include phthalic acids, adipic acid, maleic acid, trimellitic acid, itaconic acid, succinic acid, terephthalic acid, and alkenylsuccinic acid. Examples of the polyester acrylate include polyester acrylates composed of adipic acid/1,6-hexanediol/acrylic acid, phthalic anhydride/propylene oxide/acrylic acid, and trimellitic acid/diethyleneglycol/acrylic acid.

The epoxy acrylate is one which is prepared by esterifying the epoxy group of an epoxy resin with acrylic acid, thereby changing the functional group into acryloyl group. Examples of the epoxy acrylate include bisphenol-A epichlorohydrin-type epoxy resin/acrylic acid, phenol novolak epichlorohydrin-type epoxy resin/acrylic acid, and alicyclic epoxy resin/acrylic acid.

The polyurethane acrylate is obtained by reacting an isocyanate compound (such as tolylene diisocyanate) with an acrylate having a hydroxyl group (such as 2-hydroxyethyl acrylate). In this case, the acrylation takes place in such a manner that the molecule has a polyester structure at its center and isocyanate groups at its terminals.

Examples of the urethane compound include oil-modified polyurethane resin, moisture-curable polyurethane resin, block-type polyurethane resin, and catalyst-curable polyurethane resin. Examples of the epoxy compound include one which is formed by incorporating an epoxy resin with an adequate hardener, one which is formed by esterification through the reaction between an epoxy resin and a fatty acid, and one which is composed of an epoxy resin and an alkyd resin. Examples of the silicone compound include initial condensates obtained by reacting monomethyl- or monoethyltrichlorosilane with a small amount of dimethyl- or diethyldichlorosilane. The silicone compound is usually used in the form of solution in an adequate solvent containing a cure accelerator such as soluble fatty acid salt and zinc octanoate. Examples of the organotitanium compound include tetrabutoxy titanium and butyl titanate.

Diluent

Examples of the diluent include ketones such as methyl ethyl ketone, methyl isobutyl ketone, and cyclohexanone; aromatic hydrocarbons such as benzene, toluene, and xylene; halogenated hydrocarbons such as chloroform and methylene chloride; alcohols such as methanol, ethanol, propanol, and butanol; ethers such as tetrahydrofuran and dioxane; and cellosolves such as ethyl cellosolve and butyl cellosolve. They may be used alone or in combination with one another.

Preferable among these solvents are ketones and alcohols and mixed solvents thereof. Most desirable is a mixed solvent of methyl isobutyl ketone and isopropyl alcohol or butyl alcohol.

There are no specific limitations in the mixing ratio of the diluent and the phosphazene compound. The mixing ratio is usually 1:9 to 9:1 by weight. When the organic solvent and the phosphazene compound are mixed at a ratio of 9:1 to 5:5, the resulting composition has an adequate viscosity that provides good workability.

Cure accelerator

Examples of the above-mentioned cure accelerators include a photopolymerization initiator in the case where curing is accomplished by irradiation with ultraviolet rays or visible light. Examples of the photopolymerization initiator include 1-hydroxycyclohexyl phenyl ketone, dibenzoyl, benzoylmethyl ether, benzoin ethyl ether, p-chlorobenzophenone, p-methoxybenzophenone, benzoyl peroxide, di-tert-butyl peroxide, and camphor quinone. They may be used alone or in combination with one another. They are used in an amount of 0.05 to 5.0 parts by weight for 100 parts by weight of the curable compound.

In the case where polymerization is accomplished by heating or at normal temperature, the polymerization initiator is a peroxide compound, an amine compound or a mixture of.thereof. Examples of the peroxide compound include benzoyl peroxide, p-chlorobenzoyl peroxide, 2,4-dichlorobenzoyl peroxide, 2,4-dichlorobenzoyl peroxide, t-butyl hydroperoxide, di-t-butyl peroxide, dicumyl peroxide, t-butyl peroxyacetate, diacetate, and t-butyl peroxybenzoate. Examples of the amine compound include N,N-diethanol-p-toluidine, dimethyl-p-toluidine, p-toluidine, methylamine, t-butylamine, methylethylamine, diphenylamine, 4,4'-dinitrodiphenylamine, o-nitroaniline, p-bromoaniline, and 2,4,6-tribromoaniline.

The peroxide compound and amine compound are used in an amount of 0.05 to 5.0 parts by weight (in total) for 100 parts by weight of the curable compound.

Filler

Examples of the above-mentioned inorganic or organic fillers include silica, glass, metal, and ceramics in the form of powder or fiber, and also include organic fiber. Other additive that can be added include an antioxidant and UV light absorber.

The selection of filler depends on the application area in which the coated resin molded-article is used.

In the case where the coated resin molded-article is required to have good optical properties, especially transparency, the inorganic or organic filler should be one which permits the transmission of active light. Examples of such a fillers include inorganic filler such as colloidal silica and organic fillers such as polymethyl methacrylate.

In the case where the coated resin molded-article is used as magnetic recording media, such as magnetic tape and floppy disks, the filler is a magnetic powder. (In this case, the magnetic recording medium is prepared by coating a polyester substrate such as flexible polyester film, polyester sheet, and polyester tape with a magnetic layer in which the phosphazene compound functions as a binder.)

Examples of the magnetic powders include iron oxides (such as $\gamma$-iron oxide and tri-iron tetroxide), cobalt-containing $\gamma$-iron oxide, chromium oxide, pure iron, ferro-alloy (such as cobalt-iron-nickel alloy), and nickel-cobalt alloy.

If it is necessary to impart electrical conductivity to the cured coating formed from a coating material containing a curable phosphazene compound, the filler should preferably be an electrically conductive substance. Examples of the electrically conductive substance include gold, silver, copper, carbon black, and graphite.

If it is necessary to impart an ability to absorb radio waves to the cured coating formed from a coating material containing a curable phosphazene compound, the filler should preferably be manganese-zinc ferrite. In addition, to impart an ability to moderate electrolysis, the filler should preferably be a silicon carbide powder.

Other additives

The above-mentioned curable phosphazene compound or composition containing a curable phosphazene compound may have incorporated therewith, if necessary, a curable compound which includes vinyl esters of a carboxylic acid (such as vinyl acetate and vinyl stearate) and an unsaturated carboxylic acid containing an ethylenic double bond (such as fumaric acid, maleic acid, maleic anhydride, itaconic acid, and itaconic anhydride).

(3) Formation of cured coating

Coating

According to the present invention, the thus prepared curable phosphazene compound or composition containing a curable phosphazene compound is applied to a desired polyester resin substrate by any known conventional process such as spinner method, spray method, roll coater method, and dipping method Subsequently, the wet coating is freed of solvent, if the coating contains any solvent.

Curing

After application, the curable compound is cured at normal temperature, or by heating or irradiation with ultraviolet rays, electron rays, X-rays, or $\gamma$-rays. In this way, the coating is formed. Curing by irradiation with ultraviolet rays is most desirable. Irradiation should be carried out for 1 second or more, preferable 3 to 300 seconds with ultraviolet rays having a wavelength of 200 to 550 nm. The cumulative amount of light for irradiation should be 50 to 5000 mJ/cm². The curing by heating should be carried out at 100° C. or above.

The thus formed coating should preferably be 0.01 to 500 μm thick. If the coating thickness is smaller than 0.01 μm, it may not be satisfactory in mechanical performance. If its thickness is in excess of 500 μm, the coating may adversely affect the flexibility of the synthetic resin substrate if the synthetic resin is a polyester.

The thus formed coating of the curable compound is superior in adhesion to the synthetic resin substrate. It also remarkably improves the surface properties (such as hardness, scratch resistance, and blocking resistance) of the synthetic resin substrate. In addition, it is superior in mechanical, optical, thermal properties, and chemical properties. Thus the coated resin molded-article of the present invention is superior in durability owing to the cured coating formed thereon The coating can be formed on the surface of the synthetic resin substrate without previous surface treatment or primer coating It can be formed by a single application of the above-mentioned coating material Thus the coated resin molded-article of the present invention is advantageous in that it can be produced in a short time with an extremely simplified process to form the coating.

(4) Usefulness and application of the coated resin molded-article

The resin molded-article coated according to the present invention has outstanding surface properties and durability by virtue of the coating formed on the desired polyester resin substrate. Since the coating consists of a cured product of a specific curable compound superior in mechanical, optical, chemical, and thermal properties, it does not adversely affect the flexibility of the polyester resin, it has good adhesion to the polyester resin substrate, and it improves the surface hardness, scratch resistance, and block resistance of the surface of the polyester resin substrate.

The coated resin molded-article of the present invention is advantageous over the conventional one in its production cost because a coating with outstanding performance can be easily formed by a single application without primer coating which needs only a short and simple step.

The coated resin molded-article of the present invention will find use in a broad range of application areas shown below on account of its outstanding properties mentioned above.

The coated resin molded-article will find use in the area where it is necessary to improve the surface properties of resin molded articles. The applications in such an area include photomasks used for the production of ICs, printed circuits, and hybrid ICs; base film (such as lithfilm) for printing; base film for magnetic recording media; and packaging such as bottles and trays.

The coated resin molded-article will find use as containers, magnetic recording media, and heat-sensitive recording media which are explained in more detail as follows:

(a) Containers

In the case where the coated resin molded-article is based on a thermoplastic polyester resin substrate, it will find use as containers. The containers include food-packaging containers for retort foods, half-cooked foods, and drinks. The food-packaging containers may be in the form of pouch and box (e.g., flat pouch, cylindrical pouch, bottomed pouch, boxlike pack, Tetrapack, and milk pack).

Containers of such shape can be produced by heat sealing of film or thermoforming of a synthetic resin substrate in sheet or film form. The thus formed container is internally lined with the cured coating which is formed from a coating material containing the above-mentioned curable phosphazene compound. Subsequently, the container is filled with a food, and the opening of the container is tightly closed by heat sealing.

Containers in the form of bottle, tray, and cup may also be produced by injection molding, blow molding, etc. in addition to the above-mentioned thermoforming.

The container in the form of bottle has the above-mentioned cured coating formed on at least the internal surface thereof.

The containers in the form of bottle are suitable for storing liquid such as petroleum, chemicals, pesticides, and detergents.

The above-mentioned food packaging containers and bottle-like containers to store petroleum etc. are protected from attack by the contents because the internal surface in contact with the contents is covered with the cured coating formed from a coating material containing a curable phosphazene compound. In addition, they suffer only a little from degradation by environmental change. Thus they can store the contents safely.

(b) Magnetic recording media

The coated resin molded-article of the present invention, especially the coated polyester molded-article, will find use as a magnetic recording medium.

The magnetic recording medium is composed of a base film (polyester substrate) in the form of long sheet or disk and a back coating layer formed on the opposite side of the magnetic layer. The back coating layer is a cured coating formed from a coating material containing a curable phosphazene compound, and it is superior in durability, abrasion resistance, heat resistance, adhesion, and dimensional stability. This magnetic recording medium has good tape running stability and gives off no powder resulting from abrasion during tape running. Therefore, it has good electromagnetic properties The magnetic recording medium of another type is composed of a base film (polyester substrate) in the form of long sheet or disk and a magnetic layer of a cured coating formed on the surface of the base film. In this case, the cured coating is made of a coating material containing a curable phosphazene compound and a magnetic substance. The magnetic recording medium has good adhesion between the base film and the magnetic layer. In addition, the magnetic layer is superior in durability, abrasion resistance, and solvent resistance. It also permits the uniform dispersion of magnetic powder. Therefore, the magnetic recording medium is superior in magnetic recording performance.

Incidentally, the magnetic layer is formed from a magnetic composition composed of 100 parts by weight of magnetic powder, 10 to 50 parts by weight of a curable phosphazene compound, 100 to 300 parts by weight of an organic solvent and other necessary additives. This magnetic composition is applied to the base film.

(c) Heat-sensitive transfer recording medium

The coated resin molded-article of the present invention, especially the coated polyester molded-article, will find use as a heat-sensitive transfer recording medium.

The heat-sensitive recording medium is composed of a base film (polyester substrate) in the form of tape and a back coating layer formed on the opposite side of the ink layer. The back coating layer is a cured coating formed from a coating material containing a curable phosphazene compound.

The cured coating film should be 0.03 to 20 $\mu$m thick, preferably 0.05 to 5.0 $\mu$m thick from the standpoing of balance between the protecting effect and the usability of ink ribbon.

The thus formed cured coating of a curable compound has good adhesion to the base film of PET (polyethylene terephthalate) and also has good mechanical, thermal, and chemical properties. It greatly improves the ink ribbon in block resistance, lubricity, heat resistance, durability, running performance, and scratch resistance. Particularly, it is improved over conventional ones in the transfer of the coating material to the surface of the ink layer that takes place with time after winding. The cured coating effectively prevents sticking. Thus the ink ribbon provides improved printing performance (such as sharply printed letters). An additional advantage is that the coating with the above-mentioned superior protective effect can be formed by a single application without surface treatment (such as corona discharge treatment and primer coating) which was necessary in the past.

The heat-sensitive transfer recording medium with coating has extremely improved performance and durability during use as well as storage owing to the coating having the above-mentioned superior advantages. It is also advantageous in its structure as mentioned above. The ink ribbon is advantageously used for the printers of heat transfer-type and other types. (d) Glass substitute The coated resin molded-article of the present invention, especially the coated polycarbonate molded-article, will find use as a glass substitute.

Polycarbonate in the form of plate as the polyester resin substrate can be used as a glass substitute for building glazing if it is provided, on the surface thereof, with a cured coating formed from a coating material containing a curable phosphazene compound.

Such a glass substitute for building glazing is superior in abrasion resistance and weather resistance. In addition, it has the properties of not holding water droplets. Therefore, the glass substitute has a long life.

The glass substitute for building glazing can also be used as automotive window glass.

Polycarbonate as the polyester resin substrate can be made into an automotive light cover if it is molded into a light cover and the surface of the light cover is provided with a coating formed from a coating material containing a curable phosphazene compound.

Polycarbonate plate as the resin substrate can also be used as a plastic mirror if it is provided with a light reflecting layer (metallized layer) on the back side and with a cured coating formed from a coating material containing a curable phosphazene compound on the front side. The thus formed mirror is useful as a rear view mirror, fender mirror, and room mirror.

The plastic mirror is superior in oil resistance, abrasion resistance, impact resistance, fog resistance, and reflection performance. In addition, it is light in weight and can be formed into any desired shape.

The coated polycarbonate molded-article of the present invention can also be used as a cathode ray tube (such as television picture tube and color display tube) and a vacuum electron tube (such as fluorescent lamp).

Polycarbonate in tubular form as the polyester resin substrate may be made into a fluorescent lamp if it is provided with a fluorescent coating on the internal surface thereof and a cured coating formed from a coating material containing a curable phosphazene compound on the external surface thereof.

The fluorescent lamp made of the coated polycarbonate molded-article is superior in abrasion resistance, heat resistance, gas impermeability, and durability.

The coated resin molded-article can be advantageously used as a casing of an item which undergoes heating and cooling repeatedly.

The coated resin molded-article will find many uses in addition to those enumerated above.

When used in a variety of application areas, the resin molded article with coating will exhibit its outstanding performance as shown in the examples that follow.

EXAMPLES

The invention will be described in more detail with reference to the following examples. which are not intended to restrict the scope of the invention.

In the examples, the cured coating was evaluated by the following test methods.

(1) Initial adhesion

Measured according to the cross-cut adhesion test (1 mm intervals) which is repeated five times at the same spot.
100/100: No peeling
80/100: Adhesion ratio 80% (peeled 20%)
60/100: Adhesion ratio 60% (peeled 40%)

(2) Flexing properties

A test piece measuring 60 by 60 mm cut from a film sample is tightly wound around an iron core, 7 mm in diameter. After standing for 30 minutes, the appearance of the test piece is observed.
Good: No cracking and peeling.
Cracked and peeled: Partial cracking and peeling.

(3) Pencil hardness

Estimated by observing whether or not the surface of a test piece is scratched with a pencil.
5H: Not scratched with a 5H pencil, but scratched with a 6H pencil.
4H: Not scratched with a 4H pencil, but scratched with a 5H pencil.
3H: Not scratched with a 3H pencil, but scratched with a 4H pencil.
2H: Not scratched with a 2H pencil, but scratched with a 3H pencil.

(4) Taber abrasion

Determined by measuring haze before and after the abrasion test which is run by rotating the sample disk at 100 rpm under an abrading ring CS-10 (500 g). Haze is measured according to JIS K-7105 and calculated according to the following formula.

Haze (%) = A/B × 100 where A is diffusion transmission ratio (%) and B is total light transmission ratio (%).

(5) Falling sand abrasion

Determined by measuring haze before and after the abrasion test which is run by dropping 1000 g of #60 carborundum onto a test piece held inclined 45° from a height of 50 cm.

(6) Weather resistance

Judged by the visual inspection and cross-cut adhesion test of a test piece which has undergone weathering test at 63°C., 50%RH, for 2500 hours, with water spraying at a cycle of 12 minutes/60 minutes. (100/100 representing no peeling and 0/100 representing complete peeling.)

(7) Heat resistance

Judged by the visual inspection and cross-cut adhesion test (as in initial adhesion test) of a test piece which has been kept at 120° C. for 500 hours.

(8) Heat shock resistance

Judged by the visual inspection and cross-cut adhesion test of a test piece which has undergone 50 cycles of heating and cooling test. The test condition of one cycle is $-50°$ C.(2 hours) and 100° C.(2 hours).

(9) Hot water resistance

Judged by the visual inspection and cross-cut adhesion test of a test piece which has been soaked in hot water at 90° C. for 3 hours.

(10) Moisture resistance

Judged by the visual inspection and cross-cut adhesion test of a test piece which has been allowed to stand in an environment at 50° C. and 95%RH for 2000 hours.

(11) Acid resistance

Judged by the visual inspection and cross-cut adhesion test of a test piece which has been soaked in 5% HCl for 48 hours.

(12) Alkali resistance

Judged by the visual inspection and cross-cut adhesion test of a test piece which has been soaked in 5% NaOH solution for 48 hours.

(13) Fog resistance (ability to repel water droplets)

Determined by observing whether or not the surface of a test piece is clouded when the test piece is allowed to stand in a refrigerator at 10° C. for 1 hour and then removed to a room at 25° C. and 75%RH.

(14) Transparency

Determined by measuring the total light transmission (%) and the degree of Yellow Index according to JIS K-7105.

(15) Oil resistance

Judged by observing the appearance of a test piece which has been soaked in gasoline, kerosene, fuel oil, linseed oil, and coconut oil individually for 60 minutes.

(16) Surface gloss

Measured according to JIS K-7105 (for 60 specular gloss)

(17) Air barrier properties (gas impermeability)

Determined by measuring the degree of vacuum in a box made of sample plate (3 mm thick) after evacuating the box to $1 \times 10^{-6}$ mmHg and allowing the evacuated box to stand for 1 week.

MANUFACTURING EXAMPLE 1

Preparation of curable phosphazene compound (A)

Hexachlorocyclotriphosphazene (86.8 g) was dissolved in 338 g of dehydrated benzene placed in a 2-liter flask. To the benzene solution was added 310 g of pyridine and 0.23 g of hydroquinone with stirring.

Furthermore, 200 ml of 2-hydroxyethyl methacrylate was dissolved in 237 ml of benzene, and the resulting solution was added dropwise to the above-mentioned flask at 60° C. over 30 hours. The reaction product was filtered to remove pyridine hydrochloride.

The filtrate was washed with water, dried with sodium sulfate, and freed of solvent by distillation under reduced pressure. Thus there was obtained 200 g of 1,1,3, 3,5,5-hexa(methacryloylethylenedixoy)cyclotriphosphazene in the form of viscous liquid.

MANUFACTURING EXAMPLE 2

Preparation of curable phosphazene compound (B)

In a 2-liter flask equipped with a thermometer, stirrer, dropping funnel, and condenser were placed 300 ml of tetrahydrofuran and 25.5 g of metallic sodium. Then, 104.3 g (1.11 mol) of phenol was added dropwise. Reaction was carried out for 3 hours under refluxing to give phenolate.

Then, 400 ml of benzene solution containing 198 g (0.555 mol) of hexachlorocyclotriphosphazene was added dropwise to the tetrahydrofuran solution containing the phenolate. Reaction was carried out for 4 hours under refluxing.

After the reaction liquid was cooled to room temperature, 352 g (4.45 mol) of pyridine was added and then 381 g (2.45 mol) of 2-hydroxyethyl methacrylate was slowly added dropwise from the dropping funnel. Reaction was carried out at 60° C. for 20 hours. The reaction liquid was filtered to remove the solids which had separated out. The filtrate was freed of solvent by distillation under reduced pressure and the residue was completely dried. Thus there was obtained 452 g of liquid.

EXAMPLE 1

The curable phosphazene compound (A) obtained in Manufacturing Example 1 was dissolved in methyl isobutyl ketone. To the solution was added 1-hydroxycyclohexyl phenyl ketone as a photopolymerization initiator in an amount of 3 parts by weight for 100 parts by weight of the phosphazene compound (A). Thus there was obtained a coating solution.

The coating solution was applied to a polyester film (75 μm thick) by spraying. The coated polyester film was irradiated with ultraviolet rays (80 W/cm) at a distance of 15 cm so that the cumulative amount of light was 2940 mJ/cm². In this way, a 4-μm thick coating (A) was formed.

Furthermore, a 4-μm thick coating (B) was formed in the same manner as above on the internal surface of a blow molded bottle (100 mm in diameter).

EXAMPLE 2

The same procedure as in Example 1 was repeated except that the curable phosphazene (A) was replaced by the curable phosphazene (B) obtained in Manufacturing Example 2. Thus there were obtained coating (C) on film and coating (D) on bottle.

COMPARATIVE EXAMPLE 1

A coating solution was prepared from an acrylate coating material dissolved in toluene. The coating solution contains 1-hydroxycyclohexyl phenyl ketone as a photopolymerization initiator in an amount of 3 parts by weight for 100 parts by weight of said active ingredient.

The coating solution was applied to the substrate in the same manner as in Example 1. Thus there were obtained coating (E) on film and coating (F) on bottle.

The properties of the thus obtained coatings (A) to (F) are shown in Table 1.

TABLE 1

| Coating | Initial adhesion | Flexural properties | Pencil hardness |
|---|---|---|---|
| (A) | 100/100 | good | 5H |
| (B) | 100/100 | — | 5H |
| (C) | 100/100 | good | 4H |
| (D) | 100/100 | — | 4H |
| (E) | 40/100 | cracked, peeled | 2H |
| (F) | 50/100 | — | 2H |

COMPARATIVE EXAMPLE 1A

The same procedure as in Example 1 was repeated to form a cured coating except that the polyester film was replaced by a 3-mm thick polyethylene sheet, polypropylene sheet, or polystyrene sheet. The initial adhesion of all the coatings was 0/100.

MANUFACTURING EXAMPLE 3

(1) Preparation of curable phosphazene (C)

In a 1-liter flask equipped with a thermometer, stirrer, dropping funnel, and condenser were placed 58.0 g (0.167 mol) of hexachlorotriphosphazene (3PNC for short), 50 ml of toluene, and 158 g (2.0 mol) of pyridine. While stirring, 143 g (1.1 mol) of 2-hydroxyethyl methacrylate (HEMA for short) was added dropwise from the dropping funnel.

Reaction was carried out for 8 hours with stirring and heating in a hot bath at 60° C. The reaction liquid was filtered to remove the catalyst and the crystals which had separated out. The filtrate was freed of solvent by distillation under reduced pressure, and the residue was completely dried. Thus there was obtained 136 g of a yellowish liquid. (Yield: 91%)

(2) Preparation of coating material (C)

A UV-curable coating material (C) of the following composition was prepared from the curable phosphazene compound (C) obtained by the procedure (1) above.

Curable phosphazene compound (C): 50 parts by weight
2-methyl-[4-(methylthio)phenyl]-2-morpholino-1-propane : 3 parts by weight
p-dimethylaminobenzoic acid ethyl ester: 3 parts by weight
1,6-hexanediol diacrylate: 25 parts by weight

EXAMPLE 3

A container measuring 100 mm in diameter and 40 mm high was produced by air-pressure forming from a 0.7-mm thick polyethylene terephthalate sheet.

The internal surface (excluding the flange) of the container was coated with the above-mentioned coating material (C), and the coating was cured by irradiation with UV light.

The container was filled with gratin and the opening was closed with an aluminum foil by heat sealing. The closed container was heated at 120° C. for 3 hours.

Despite heating, the container remained unchanged in shape. After emptying, the internal surface of the container was observed to find nothing abnormal.

COMPARATIVE EXAMPLE 2

The same procedure as in Example 3 was repeated except that the coating material was not applied. After heating, the internal surface of the container easily peeled off, giving off powder, upon rubbing.

EXAMPLE 4

A cured coating was formed on the internal surface of a commercial blow molded polyester bottle (1 liter) by filling the bottle with the coating material (D) of the following formulation and then emptying the bottle, followed by heating at 80° C. for 1 hour.

Curable phosphazene compound: 100 parts by weight
Mixed solvent of methyl isobutyl ketone and ethyl alcohol: 900 parts by weight.
Methyl ethyl ketone peroxide: 1 part by weight Each of the container with cured coating was filled with gasoline, 5 wt% HCl, and 5 wt% NaOH aqueous solution. After standing for 10 days, no change occurred on the internal surface of the container and the cured coating did not peel off.

MANUFACTURING EXAMPLE 4

Preparation of coating material (E)

Coating material (E) was prepared from the curable phosphazene compound (A) obtained in Manufacturing Example 1, 700 g mixed solvent of methyl isobutyl ketone and ethyl alcohol, and 6 g of benzophenone as a photopolymerization initiator.

MANUFACTURING EXAMPLE 5

Preparation of coating material (F)

Coating material (F) was prepared from the curable phosphazene compound (B) obtained in Manufacturing Example 2, in the same manner as in Manufacturing Example 4.

EXAMPLE 5

The coating material (E) was applied by spraying to the substrates shown in Table 2. The coating was irradiated with ultraviolet rays (80 W/cm) at a distance of 15 cm so that the cumulative amount of light was 2940 mJ/cm². In this way, a 7-μm thick cured coating was formed.

TABLE 2

| Polyester film | 300 mm × 300 mm × 250 μm |
|---|---|
| Polycarbonate plate | 300 mm × 300 mm × 3 mm |

The cured coating (E) was evaluated according to the above-mentioned methods. The results are shown in Table 3.

EXAMPLE 6

The same procedure as in Example 5 was repeated except that the coating material (E) was replaced by the coating material (F) obtained in Manufacturing Example 5. The thus formed cured coating (F) was evaluated. The results are shown in Table 3.

COMPARATIVE EXAMPLE 3

A commercial acryl-based hard coating material was dissolved in butyl acetate, and the solution was applied to the substrate by spraying. Upon irradiation with ultraviolet rays (3000 mJ/cm$^2$), there was obtained a 7-$\mu$m thick cured coating. The cured coating was evaluated in the same manner as in Example 5. The results are shown in Table 3.

TABLE 3

| Items | Example 5 PET & PC | Example 6 PET & PC | Comparative Example 3 PET | Comparative Example 3 PC |
|---|---|---|---|---|
| Taber abrasion | 18% | 4% | 19% | 19% |
| Falling sand abrasion | 23% | 8% | 25% | 25% |
| Weather resistance | No change (100/100) | No change (100/100) | Cracked and peeled after 2500 hours | Peeled after 500 hours |
| Initial adhesion | 100/100 | 100/100 | 100/100 | 100/100 |
| Heat resistance | No change (100/100) | No change (100/100) | No change | Peeled after 24 hours |
| Heat shock resistance | No change (100/100) | No change (100/100) | — | — |
| Hot water resistance | No change (100/100) | No change (100/100) | — | — |
| Moisture resistance | No change (100/100) | No change (100/100) | — | — |
| Acid resistance | No change (100/100) | No change (100/100) | No change | No change |
| Alkali resistance | No change (100/100) | No change (100/100) | No change | Clouded and peeled |

Note:
"No change" means that nothing anomalous occurred in the coating appearance. "PET" and "PC" denote a polyester substrate and polycarbonate substrate, respectively. In Comparative Example 3, some items could not be evaluated because no desired results were obtained.

EXAMPLE 7

The coating material (C) was applied by spraying to the polyester film shown in Table 2 to give a coated film with a 10-$\mu$m thick coating. The gas permeability of the coated film was evaluated. The results are shown in Table 4.

COMPARATIVE EXAMPLE 4

The gas permeability of a commercial aluminum-metallized composite film (polyester and biaxially oriented polypropylene) was evaluated in the same manner as in Example 5. The results are shown in Table 4.

TABLE 4

| | Water vapor permeability | Oxygen gas permeability |
|---|---|---|
| Example 7 (Coated film) | 0.09 | 0.10 |
| Comparative Example 4 (Commercial film) | 0.16 | 0.15 |

Unit:
water vapor: g/m$^2$ · 24 hrs · 25° C. · 80% RH
oxygen gas: cc/m$^2$ · 24 hrs · 35° C. · 80% RH

EXAMPLE 8

The coating material (E) was applied to a 75-$\mu$m thick polyester film in the same manner as in Example 5. Thus there was obtained a 80-$\mu$m thick coated sheet. This coated sheet was made into a bag, with the coated side inside, for food packaging. The bag was filled with a food shown in Table 5, and then sealed, with air inside replaced by nitrogen. The sealed bag was kept at 25° C. and 80%RH in a constant temperature, constant humidity bath, to evaluate the fragrancy keeping ability. The results are shown in Table 5.

COMPARATIVE EXAMPLE 5

The polyester film used in Example 8 (non-coated base film) was made into a food packaging container, and the fragrancy keeping ability of the packaging container was evaluated in the same manner as in Example 8. The results are shown in Table 5.

TABLE 5

| Foods | Example 8 | Comparative Example 5 |
|---|---|---|
| Soy sauce | >4 | (1) |
| Sauce | >4 | (1) |
| Cocoa | >4 | >4 |
| Curry powder | >4 | 1 |
| Flakes of dried bonito | >4 | 2 |
| Powdered juice | >4 | 3 |
| Dry milk | >4 | 3 |
| Orange flavor | >4 | >4 |
| Lemon flavor | >4 | 2 |

Remarks:
The numerals in the figure indicate the time which elapsed before the food decreased in flavor or changed in quality.
(1): within one week
1: after one week
2: after two weeks
3: after three weeks
>4: no change after four weeks It is noted from the above-mentioned examples that the container with a cured coating of a curable phosphazene compound is greatly improved in surface hardness, scratch resistance, blocking resistance, toughness, transparency, chemical resistance, heat resistance, low-temperature resistance, and gas barrier properties, without any adverse effect on the inherent flexibility of the substrate, owing to the coating which has good adhesion to the substrate.

The container with cured coating can be produced in short, simple steps because the coating is formed by a single application of a coating material, without primer coating. This is advantageous in production cost over the conventional process.

EXAMPLE 9

In methyl isobutyl ketone was dissolved 100 parts by weight of the curable phosphazene compound (A) obtained in Manufacturing Example 1. To the solution was added 40 parts by weight (as solids) of silica dispersed in isopropyl alcohol. Further, 3 parts by weight of photopolymerization initiator (1-hydroxycyclohexyl phenyl ketone) was added.

The thus prepared coating solution was applied, using a roll coater, to one side of an about 8 μm thick PET ink ribbon. The wet coating was irradiated with ultraviolet rays so that the cumulative amount of light was 1500 mJ/cm². Thus there was obtained a 1-μm thick cured coating (I). The performance of the ink ribbon is shown in Table 6.

EXAMPLE 10

A coating solution was prepared by adding 2 parts by weight of fluoro-lubricant to the coating solution prepared in Example 9. The thus prepared coating solution was applied to the substrate in the same manner as in Example 9, followed by curing. Thus there was obtained a cured coating (II). The performance of the ink ribbon is shown in Table 6.

EXAMPLE 11

The same procedure as in Example 9 was repeated to give a cured coating (III) except that the curable phosphazene compound (A) was replaced by the curable phosphazene compound (B) obtained in Manufacturing Example 2. The performance of the ink ribbon is shown in Table 6.

EXAMPLE 12

A coating solution was prepared by adding 2 parts by weight of fluoro-lubricant to the coating solution prepared in Example 11. The thus prepared coating solution was applied to the substrate, followed by curing, in the same manner as above, to give a cured coating (IV). The performance of the ink ribbon is shown in Table 6.

COMPARATIVE EXAMPLE 6

To a toluene solution of a commercial acryl-based coating material was added 100 parts by weight (as active ingredient) of colloidal silica dispersed in toluene. To the solution was further added 2 parts by weight of fluoro-lubricant and 3 parts by weight of photopolymerization initiator (1-hydroxycyclohexyl phenyl ketone). The thus obtained coating solution was applied, followed by curing, in the same manner as above. Thus there was obtained a cured coating (V). The performance of the ink ribbon is shown in Table 6.

COMPARATIVE EXAMPLE 7

A commercial ink ribbon coated with a silicone coating material was evaluated. The results are shown in Table 6.

tance, and scratch resistance. The cured coating effectively prevents blocking and sticking. The ingredient in the coating does not migrate to the ink layer while the ink ribbon is stored in the wound state. This prevents the printing head being stained. An additional advantage in production is that the cured coating can be formed in a single step which does not need surface treatment such as corona discharge treatment and primer coating.

Preparation

Coating solution (a)

Curable phosphazene compound (A): 100 parts by weight
Silicone lubricant: 0.5 parts by weight
2-methyl-[4-(methylthio)phenyl]-2-morpholino-1-propanone: 3 parts by weight
Solvent: methyl isobutyl ketone Coating solution (b)

Curable phosphazene compound (B): 100 parts by weight
Silicone lubricant: 0.2 parts by weight
2-methyl-[4-(methylthio)phenyl]-2-morpholino-1-propane: 3 parts by weight
Solvent: methyl isobutyl ketone

EXAMPLE 13

The coating solution (a) containing 10 wt% solids was applied to polyethylene terephthalate (PET) film for video tape (ultrasmooth type) using a gravure coater. Upon irradiation with ultraviolet rays, there was obtained PET film tape with a 0.5-μm thick back coating. This tape underwent various tests.

EXAMPLE 14

The same procedure as in Example 13 was repeated except that the coating solution (b) containing 10 wt% solids was used. Thus there was obtained a PET film with a back coating. The tape underwent various tests.

COMPARATIVE EXAMPLE 8

The PET film video tape (ultrasmooth type) without back coating underwent various tests.

COMPARATIVE EXAMPLE 9

A commercial tape with back coating underwent various tests.

TABLE 6

| Item | Example 9 (I) | Example 10 (II) | Example 11 (III) | Example 12 (IV) | Comparative Example 6 (V) | Comparative Example 7 |
|---|---|---|---|---|---|---|
| Adhesion*¹ | good | good | good | good | partially peeled | good |
| Running performance*² | good | good | good | good | poor | good |
| Heat resistance*² | good | good | good | good | peeled | good |
| Head staining*² | none | none | none | none | stained with peeled coating | none |
| Printed letters*² | good | good | good | good | all letters blurred | blurred every 40-50 letters |

*¹Evaluated by winding the tape onto a cassette
*²Evaluated by actual printing with inked tape wound onto a cassette.

It is noted from Table 6 that the secured coating as the backing layer formed on the back of the base film of ink ribbon has good adhesion to the base film such as PET film. Owing to this cured coating, the ink ribbon is superior in heat resistance, lubricity, blocking resis-

COMPARATIVE EXAMPLE 10

A commercial tape without back coating underwent various tests.

Figure 2:
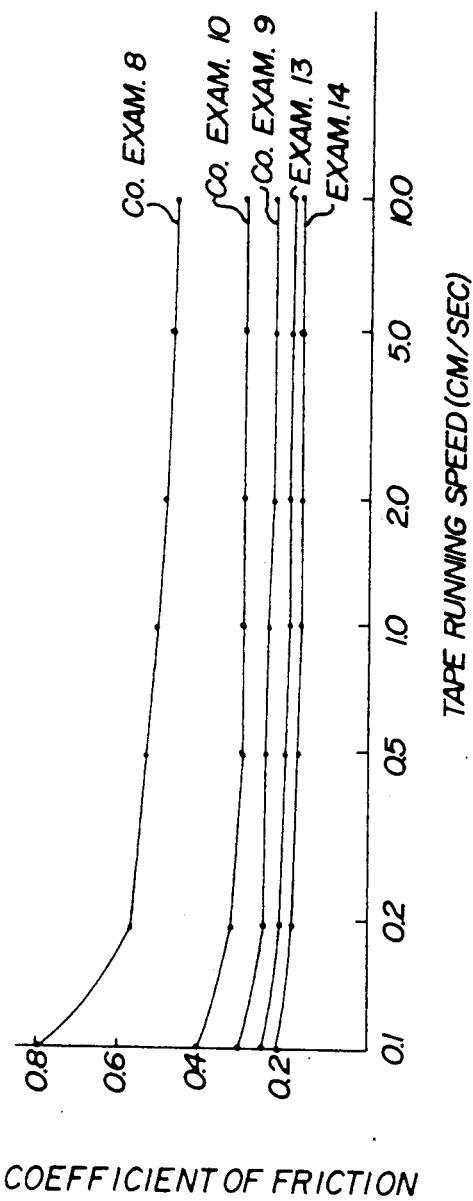

The test results of the film tape mentioned above are shown in Table 7 and FIGS. 1 and 2. FIG. 1 shows data which were obtained when the tape was run at 1.0 cm/sec. FIG. 2 shows data which were obtained after 1500 runs. The test methods are as follows:

(1) Coefficient of friction

Figure 3:
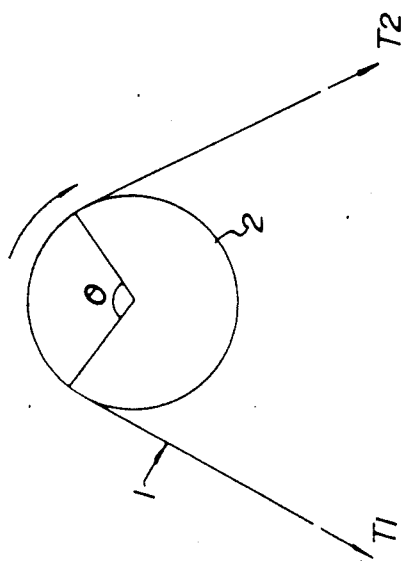
FIG. 3 is a schematic representation of an apparatus used for measuring the coefficient of friction in examples and comparative examples.

The tape 1 is run along the cylindrical drum 2 as shown in FIG. 3. The tension ($T_2$) in the running direction and the tension ($T_1$) in the direction opposite to the running direction are measured. The angle (8) of the arc in contact with the running tape is measured. The coefficient of friction ($\mu$) is calculated from the following formula.

$$\mu = (1/\theta) \times \ln(T_1/T_2)$$

where ln denotes the natural logarithm.

(2) Abrasion resistance

Determined by measuring the weight of the tape before and after 2000 runs.

(3) Dimensional change

Expressed by the change that takes place when the tape is heated from 25° C. to 75° C.

TABLE 7

| Items | Example 13 | Example 14 | Comparative Example 8 | Comparative Example 9 | Comparative Example 10 |
| --- | --- | --- | --- | --- | --- |
| Abrasion resistance (%) | <0.01 | 0.02 | 0.03 | 0.10 | 0.15 |
| Dimensional change (%) | 0.05 | 0.04 | 0.15 | 0.14 | 0.14 |

It is noted that the magnetic tape has very good dimensional stability (very little elongation on heating) and a very small coefficient of friction on account of the back coating which has a low coefficient of friction and is superior in durability, abrasion resistance, heat resistance, adhesion, and dimensional stability. An additional advantage of the magnetic tape is that it retains the same coefficient of friction after repeated use, provides good running stability, and has good scratch resistance (giving off no fine powder resulting from friction). Consequently, this magnetic tape is very useful as video and audio magnetic tape.

MANUFACTURING EXAMPLE 6

(1) Preparation of curable phosphazene compound (G)

In a 1-liter flask equipped with a thermometer, stirrer, dropping funnel, and condenser were placed 100 ml of tetrahydrofuran and 11.6 g (0.5 mol) of metallic sodium. Further, 55.5 g (0.55 mol) of 2,2,2-trifluroethanol was added dropwise. Reaction was carried out under refluxing until sodium disappeared. To the reaction solution was added dropwise 100 ml of toluene solution containing 39.6 g (0.111 mol) of 3PNC. Reaction was carried out for 2 hours under refluxing. To the reaction solution cooled to room temperature was added dropwise 191 g (1.47 mol) of HEMA from the dropping funnel. Then, the reactants were heated to 60° C. on a hot bath and stirred at that temperature for 8 hours. The reaction liquid was filtered to remove catalyst and crystals which had separated out. The filtrate was freed of solvent by distillation under reduced pressure. The residue was dried completely. Thus there was obtained 88 g of a yellowish liquid. (Yield: 93%)

(2) Preparation of coating material (G)

A UV-curable coating material (G) of the following composition was prepared from the curable phosphazene compound (G) obtained in the procedure (1) above.

Curable phosphazene compound (G) ... 30 g
Isopropyl alcohol ... 20 g
Methyl isobutyl ketone ... 30 g
Butanol ... 20 g
1-hydroxycyclohexyl phenyl ketone (initiator) ... 1 g

EXAMPLE 15

The UV light curable coating material (E) obtained in Manufacturing Example 6 was applied to a polycarbonate plate (120×120×3 mm) to form a 5-$\mu$m thick coating. The wet coating was irradiated with UV light (80 W) at a distance of 15 cm so that the cumulative amount of light was 2940 mJ/cm$^2$, while the polycarbonate plate was being transferred at a rate of 1 m/min by a belt conveyor. Thus there was formed a cured coating (E). The polycarbonate plate with the cured coating (E) was tested for various physical properties. The results are shown in Table 8.

EXAMPLE 16

The same procedure as in Example 15 was repeated except that the UV curable coating material (E) was replaced by the UV curable coating material (G) obtained in Manufacturing Example 6. Thus there was formed a cured coating (G) on the polycarbonate plate. The polycarbonate plate with the cured coating (G) was tested for various physical properties. The results are shown in Table 8.

COMPARATIVE EXAMPLE 11

The same procedure as in Example 15 was repeated to form a cured coating (H) on the polycarbonate plate, except that the UV curable coating material (E) was replaced by a commercial silicone coating material and the UV curing was replace by heat curing at 90° C. for 1 hour. The polycarbonate plate with the secured coating (H) was tested for various physical properties. The results are shown in Table 8.

COMPARATIVE EXAMPLE 12

The same procedure as in Example 15 was repeated to form a cured coating (I) on the polycarbonate plate, except that the UV curable coating material (E) was replaced by a commercial acrylic coating material. The polycarbonate plate with the cured coating (I) was tested for various physical properties. The results are shown in Table 8.

TABLE 8

| Items | Example 15 Coating (E) | Example 16 Coating (G) | Comparative Example 11 Coating (H) | Comparative Example 12 Coating (I) |
|---|---|---|---|---|
| Taber abrasion | 6% | 4% | | |
| Falling sand abrasion | 9% | 8% | | |
| Weather resistance | No change (100/100) | No change (100/100) | Peeled after 500 hours | Severely degraded after 350 hours |
| Initial adhesion | 100/100 | 100/100 | 100/100 | 100/100 |
| Heat resistance | No change (100/100) | No change (100/100) | Peeled after 24 hours | Peeled after 24 hours |
| Heat shock resistance | No change (100/100) | No change (100/100) | No change | Yellowed |
| Hot water resistance | No change (100/100) | No change (100/100) | No change | Yellowed |
| Moisture resistance | No change (100/100) | No change (100/100) | No change | Yellowed |
| Acid resistance | No change (100/100) | No change (100/100) | No change | No change |
| Alkali resistance | No change (100/100) | No change (100/100) | Clouded and peeled | Clouded (100/100) |
| Waterdrop repellency | No cloud (100/100) | No cloud (100/100) | Clouded | Clouded |
| Impact resistance | No cracks (in 20 pieces tested) | No cracks (in 20 pieces tested) | Cracks in 17 pieces of 20 pieces tested | Cracks in 19 pieces of 20 pieces tested |
| Cloud resistance | No cloud | No cloud | Clouded | Clouded |
| Transparency* | 92.0% (0.4) | 91.8% (0.3) | 90.3% (0.8) | 88.4% (1.2) |
| Oil resistance | No change | No change | No change | Partially peeled |
| Surface gloss | 150 | 135 | 95 | 96 |
| Air barrier properties | Vacuum kept | Vacuum kept | Vacuum lost | Vacuum lost |

Note:
"No change" means that nothing anomalous occurred in the coating apperance. Transparency is indicated by the total light transmission (%) and the degree of yellowness.

It is noted from Table 8 that the coated polycarbonate molded-article is superior to the conventional one in abrasion resistance, weather resistance, heat resistance, heat shock resistance, hot water resistance, moisture resistance, acid resistance, alkali resistance, impact resistance, cloud resistance, transparency, oil resistance, surface gloss, and air barrier properties. It meets all the requirements of glass substitute used for building glazing, automotive window glass, light cover, and mirror, and vacuum electron tubes. It has good durability, too.

We claim:

1. A coated resin molded-article which comprises a polyester resin · substrate and an adherent coating thereon which consists essentially of a curable phosphazene compound represented by the formula $$-[NP(X)_p(Y)_q]_n- \quad (I)$$

wherein X and Y denote a polymerizable-curable group or non-polymerizable-curable group, which are identical or different, at least one of them being a polymerizable-curable group; p and q each denote a numeral of at least 0, their sum being 2; and n is an integer of 3 to 12.

2. A coated resin molded-article as claimed in claim 1, wherein the polyester resin is a member selected from the group consisting of polyethylene terephthalate, polybutylene terephthalate, polycarbonate, and polyester carbonate.

3. A coated resin molded-article as claimed in claim 1, wherein the polymerizable-curable group is at least one member selected from the group consisting of acryloyl group, methacyloyl group, vinyl group, and allyl group, and the non-polymerizable-curable group is at least one member selected from the group consisting of phenoxy group, halogenated phenoxy group, alkoxy group, halogenated alkoxy group, alkylamino group, halogen group and halogenated alkylamino group.

4. A coated resin molded-article as claimed in claim 1, wherein the X and Y are an acryloyloxy group or methacryloyloxy group represented by the formula (II) below.

$$-ORO_2C-\overset{Z}{\underset{|}{C}}=CH_2 \quad (II)$$

where R denotes an alkylene group having 1 to 12 carbon atoms, and Z denotes a hydrogen atom or methyl group.

5. A coated resin molded-article as claimed in claim 1, wherein the polyester resin substrate is a polyester film, the coating comprises a magnetic layer containing magnetic powder, and the coated resin molded-article is a magnetic recording medium.

6. A coated resin molded-article as claimed in claim 1, wherein the polyester resin substrate is a polyester film, the coating is a back coat layer, and the coated resin molded-article is a heat sensitive transfer recording medium.

7. A coated resin molded-article as claimed in claim 1, wherein the polyester resin substrate is polycarbonate and the coated resin molded-article is a glass substitute.

8. A coated resin molded-article as claimed in claim 1, wherein the coated resin molded-article is a container obtained by injection molding, blow molding, or thermoforming.

* * * * *